(12) United States Patent
Xu et al.

(10) Patent No.: US 11,242,502 B2
(45) Date of Patent: Feb. 8, 2022

(54) **LOW UREA-PRODUCING AND FLAVOR-PRODUCING *WICKERHAMOMYCES ANOMALUS* STRAIN AND USE THEREOF IN FOOD PRODUCTION**

(71) Applicant: Jiangnan University, Wuxi (CN)

(72) Inventors: Yan Xu, Wuxi (CN); Qun Wu, Wuxi (CN)

(73) Assignee: Jiangnan University, Wuxi (CN)

( * ) Notice: Subject to any disclaimer, the term of this patent is extended or adjusted under 35 U.S.C. 154(b) by 110 days.

(21) Appl. No.: 16/218,246

(22) Filed: Dec. 12, 2018

(65) Prior Publication Data

US 2019/0112677 A1    Apr. 18, 2019

Related U.S. Application Data

(63) Continuation of application No. PCT/CN2017/082103, filed on Apr. 27, 2017.

(30) Foreign Application Priority Data

Jun. 14, 2016 (CN) .......................... 201610415338.2

(51) Int. Cl.
| | |
|---|---|
| *A23L 33/14* | (2016.01) |
| *C12G 3/02* | (2019.01) |
| *C12G 3/021* | (2019.01) |
| *C12G 3/022* | (2019.01) |
| *C12H 6/02* | (2019.01) |
| *C12N 1/16* | (2006.01) |
| *C12N 1/14* | (2006.01) |
| *C12R 1/84* | (2006.01) |
| *C12R 1/645* | (2006.01) |

(52) U.S. Cl.
CPC .............. *C12G 3/021* (2019.02); *A23L 33/14* (2016.08); *C12G 3/022* (2019.02); *C12H 6/02* (2019.02); *C12N 1/145* (2021.05); *C12N 1/16* (2013.01); *C12N 1/165* (2021.05); *C12R 2001/645* (2021.05); *C12R 2001/84* (2021.05)

(58) Field of Classification Search
None
See application file for complete search history.

(56) References Cited

FOREIGN PATENT DOCUMENTS

| | | |
|---|---|---|
| CN | 103184167 A | 7/2013 |
| CN | 105861346 A | 8/2016 |

OTHER PUBLICATIONS

Walker, G.M., Antonie van Leeuwenhoek, vol. 99, pp. 25-34 (2011). (Year: 2011).*
Yuxing et al., CN103184167; 2015; English machine translation (2015). (Year: 2015).*
Yuxing et al., CN103184167; 2015; English machine translation (2015; of record). (Year: 2015).*
Walker, G.M., Antonie van Leeuwenhoek, vol. 99, pp. 25-34 (2011; of record) . (Year: 2011).*
Huang, Duhou, "Breeding of Chinese Rice Wine Yeast Saccharomyces Cerevisiae", China Masters Theses Full Text Database, No. 2, Feb. 15, 2014(Feb. 15, 2014), ISSN: 1674-0246, see the whole document.

* cited by examiner

*Primary Examiner* — Soren Harward
*Assistant Examiner* — Paul D Pyla
(74) *Attorney, Agent, or Firm* — IPro, PLLC

(57) ABSTRACT

The present invention discloses a low urea-producing and flavor-producing *Wickerhamomyces anomalus* strain and a use thereof in food production, falling within the fields of wine brewing and food safety. The *Wickerhamomyces anomalus* of the present invention is obtained by isolating from a liquor fermentation environment (Daqu), is named *Wickerhamomyces anomalus* CGMCC NO. 12416, and was deposited at China General Microbiological Culture Collection Center on May 6, 2016, with a deposit number of CGMCC NO. 12416. The strain of the present invention has the characteristics of low urea production, flavor production, and tolerance to ethanol and acids, is an excellent strain having a fermentation function, and can be used in brewed wine, distilled liquor and other food fields to ensure food safety.

3 Claims, 1 Drawing Sheet

LOW UREA-PRODUCING AND FLAVOR-PRODUCING *WICKERHAMOMYCES ANOMALUS* STRAIN AND USE THEREOF IN FOOD PRODUCTION

TECHNICAL FIELD

The disclosure herein relates to a low urea-producing and flavor-producing *Wickerhamomyces anomalus* strain and a use thereof in food production, falling within the fields of wine brewing and food safety.

BACKGROUND

Traditional food may inevitably contain a metabolic by-product, namely ethyl carbamate (EC) in a fermentation process. EC is produced by microbial metabolism in a fermentation process or is formed by a spontaneous chemical reaction between urea, citrulline and the like in raw materials and ethanol. Precusor substances for the formation of EC mainly include urea, cyanide and citrulline, wherein urea is a main precursor substance, such as yellow rice wine and wine, currently accepted for the formation of EC in alcoholic beverages. It has been proved that a main precursor for the formation of EC in a Chinese liquor fermentation process is urea, the content thereof in fermented grains being 26 to 80 mg/kg.

Urea is mainly produced by yeast metabolism of arginine. Because most foreign alcoholic beverages are fermented by a single bacterium or are co-fermented by a few strains, *Saccharomyces cerevisiae* plays a major role in a fermentation process. Therefore, most studies focus on *Saccharomyces cerevisiae,* and it is concluded that *Saccharomyces cerevisiae* is a main strain for urea production in alcoholic beverages. However, many fermented foods belong to multi-strain fermentations. In addition to *Saccharomyces cerevisiae,* non-*Saccharomyces cerevisiae* is involved, and plays an important role in the fermentation process. *Wickerhamomyces anomalus* has the characteristic of producing various esters in the fermentation process, and is an important precursor for the formation of various wines, and *Wickerhamomyces anomalus* is an important strain in a food production process. Therefore, in the fermentation process, the flavor of food may be improved by adding a *Wickerhamomyces anomalus* strain. For example, during the production of sesame-flavored Chinese liquor, yeast bran starter may improve the flavor by adding *Wickerhamomyces anomalus.*

Recent studies have found that *Wickerhamomyces anomalus* is an important urea-producing strain. A large amount of urea produced during the fermentation process will lead to the formation of EC in the fermentation process, thereby resulting in the problem of safety. Therefore, acquisition of *Wickerhamomyces anomalus* strain, which has low urea production, has a flavor-producing function and can be adaptive to various food production environments, is particularly important for the production of fermented food with yeast serving as a main functional microorganism, and has an important contribution to food safety.

SUMMARY

In order to solve the foregoing problems, the present invention provides a low urea-producing *Wickerhamomyces anomalus* CGMCC NO. 12416 strain, obtained by screening from various flavored liquor fermentation environments. The strain, obtained from a Chinese liquor fermentation process, has the characteristics of flavor production, ethanol production, tolerance to acids and the like, is an excellent strain having a fermentation function, and can be effectively used in making brewed wine, distilled liquor, compound wine and other fermented foods, so as to reduce the formation of urea and EC in a food fermentation process, thereby solving the problem of food safety.

A first objective of the present invention is to provide a *Wickerhamomyces anomalus* CGMCC NO. 12416 strain, deposited at China General Microbiological Culture Collection Center on May 6, 2016, with a deposit number of CGMCC NO. 12416.

The *Wickerhamomyces anomalus* CGMCC NO. 12416 strain is obtained by isolating and screening from a natural fermentation process of Chinese liquor.

The *Wickerhamomyces anomalus* CGMCC NO. 12416 strain has low urea production, has a flavor-producing function and can be adaptive to a food production environment.

The *Wickerhamomyces anomalus* CGMCC NO. 12416 strain may be cultured in all media suitable for the growth of yeast (wherein colonies are grown on a WL solid medium as shown in FIG. 1). A culture mode is static culture or shaking culture, wherein the temperature is in a range of 4 to 46° C., and the culture time is sufficient for the growth of microorganisms.

After the *Wickerhamomyces anomalus* CGMCC NO. 12416 strain is fermented by a sorghum medium for 48 h, alcohols in metabolic flavor substances reach 11365.08 µg/L, esters reach 23905.69 µg/L, ketones reach 259.32 µg/L, aldehydes reach 176.95 µg/L, benzene rings reach 4623.65 µg/L, acids reach 165.23 µg/L, and terpenes reach 150.23 µg/L, wherein among main flavor substances, the contents of alcohols and esters are the most, where alcohols such as 3-methyl-1-butanol, phenylethanol and 2-methyl-1-propanol are the most, and in esters, the content of ethyl acetate is the most, followed by 2-phenylethyl acetate, ethyl propionate, ethyl caproate and the like.

The *Wickerhamomyces anomalus* CGMCC NO. 12416 strain has a growth temperature in a range of 4 to 46° C., a suitable temperature of 25 to 42° C., and a growth pH in a range of 2.3 to 12.0, preferably 4.0 to 8.0, and may be grown in an environment containing 60% of glucose, 2.0% of KCl and 12% of ethanol.

A second objective of the present invention is to provide a microbial inoculant containing the *Wickerhamomyces anomalus* CGMCC NO. 12416 strain.

In one embodiment of the present invention, the microbial inoculant contains living cells of *Wickerhamomyces anomalus* CGMCC NO. 12416 thalli, freeze-dried *Wickerhamomyces anomalus* CGMCC NO. 12416 dry thalli, immobilized *Wickerhamomyces anomalus* CGMCC NO. 12416 cells, a liquid inoculant of *Wickerhamomyces anomalus* CGMCC No. 12416, a solid inoculant of *Wickerhamomyces anomalus* CGMCC No. 12416, or a *Wickerhamomyces anomalus* CGMCC No. 12416 strain in any other form. *Wickerhamomyces anomalus* CGMCC NO. 12416 strains in these forms can all be cultured at an ethanol concentration of 0 to 14%, a temperature of 10 to 42° C., a sugar concentration of 0 to 60% and a pH of 2.3 to 11, and can produce flavors.

In one embodiment of the present invention, the microbial inoculant further contains strains of any species, applicable to food or food preparation, such as *Bacillus licheniformis, Saccharomyces cerevisiae* and *Bacillus subtilis.*

In one embodiment of the present invention, the microbial inoculant further contains any carrier available for food.

In one embodiment of the present invention, a preparation method for the liquid inoculant of *Wickerhamomyces anomalus* CGMCC No. 12416 includes: inoculating a *Wickerhamomyces anomalus* CGMCC No. 12416 strain in a liquid yeast inoculant medium, and culturing for 24 h at 30° C., a recipe for the liquid yeast inoculant medium being A or B, wherein A: 10 g/L of yeast extract, 20 g/L of peptone, 20 g/L of glucose, and the balance of water are contained.

B: Raw materials used for Chinese liquor fermentation are medium components. After the raw materials are crushed, the raw materials are mixed in a ratio of the raw materials to water being 1:1 to 1:4 w/v, and are cooked for 1 to 5 h. After cooling, a raw material namely 10 to 50 units/g of glucoamylase is added, an obtained material is kept for 2 to 10 h at 40 to 80° C., and is filtered and centrifuged to obtain filtrate, a sugar content is adjusted to 10 to 150 Bx, and a pH is adjusted to 4 to 6, wherein the raw materials are any one or a mixture of more of sorghum, barley, wheat, peas and bran in any proportion.

In one embodiment of the present invention, a preparation method for the solid inoculant of *Wickerhamomyces anomalus* CGMCC No. 12416 includes: inoculating an activated strain in a solid yeast inoculant medium in an inoculation ratio of 10%, and culturing for 24 to 36 h at 30° C., a recipe for the solid yeast inoculant medium being C or D, wherein C: Raw materials are any one or a mixture of more of sorghum, barley, wheat, peas and bran in any proportion, and after the raw materials are crushed, the raw materials are mixed in a ratio of the raw materials to water being 1:0.5 to 1:2 w/v, and are cooked for 30 min at 80 to 100° C.

D: Fermentation materials obtained from any one or a mixture of more of sorghum, barley, wheat, peas and bran in any proportion are kept for 2 to 10 h at 40 to 80° C., 0.1 to 1 mol/L of NaOH solution is added, and acidity is adjusted to 0-5.

A third objective of the present invention is to provide a use of the *Wickerhamomyces anomalus* CGMCC NO. 12416 strain, which is used in the technical field of food, particularly in the technical field of fermented food.

The use refers to a use in brewed wine, distilled Chinese liquor and the like, such as liquor, wine, yellow rice wine and fruit wine, particularly sesame-flavored bran starter liquor.

The use refers to addition of the *Wickerhamomyces anomalus* CGMCC NO. 12416 strain to a fermentation process of Chinese liquor, wine, yellow rice wine or fruit wine.

The use refers to addition of the *Wickerhamomyces anomalus* CGMCC NO. 12416 strain into a seed (starter or seed culture solution), such as addition into yeast bran starter.

A fourth objective of the present invention is to provide a method for reducing EC. The method includes: adding a *Wickerhamomyces anomalus* CGMCC NO. 12416 strain to a food preparation process.

The present invention has the beneficial effects as follows.

The present invention obtains a *Wickerhamomyces anomalus* strain, which has low urea production, flavor production and tolerance to ethanol and acids. The use of the yeast in brewed wine, distilled liquor and other food fields may reduce the formation of urea and EC to a certain extent. The strain of the present invention may be grown in environments respectively containing 60% of glucose, 2.0% of KCl and 12% of ethanol. The yield of urea is much lower than that of other existing *Wickerhamomyces anomalus* strains, and the ability of flavor production is strong. A maximum value of urea production in a fermentation process of the strain of the present invention is 351.23 μg/L, much lower than that of other strains of the same species. For example, a maximum value of a type strain is 3339.15 μg/L.

DETAILED DESCRIPTION

Embodiment 1: Screening and Identification of Low Urea-Producing *Wickerhamomyces anomalus*

Figure 1:
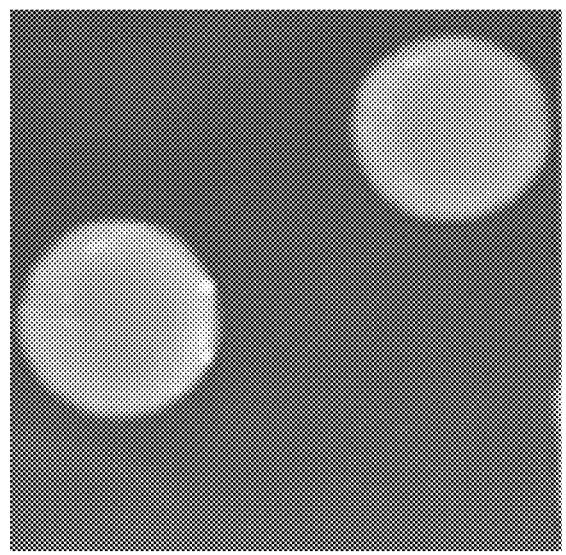
FIG. 1 shows a colonial morphology of *Wickerhamomyces anomalus* CGMCC NO. 12416 on a WL medium.
Figure 2:
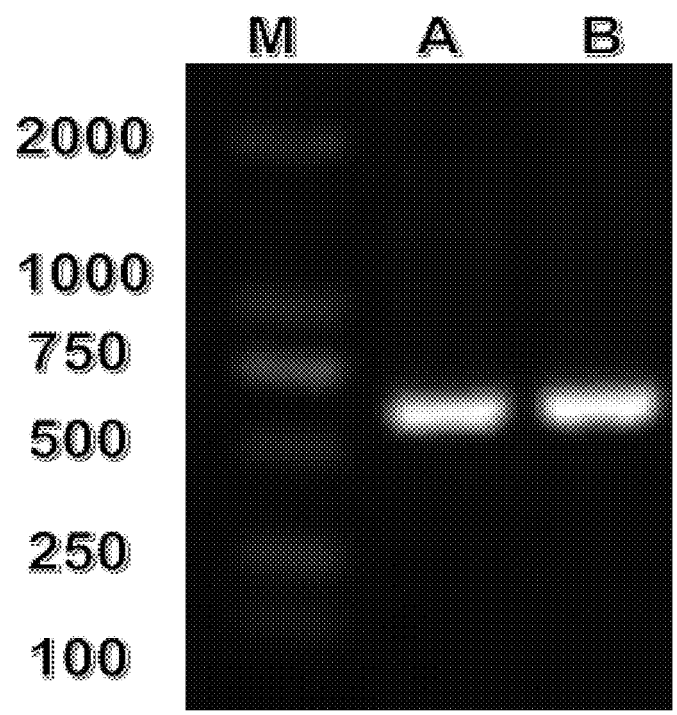
FIG. 2 shows a 26S rDNA amplification gel electrophoresis diagram of *Wickerhamomyces anomalus* CGMCC NO. 12416, where A is an amplification result of a type strain *Wickerhamomyces anomaus* 21886 (China General Microbiological Culture Collection Center), B is an amplification result of *Wickerhamomyces anomalus* CGMCC NO. 12416, and M is a 2000DL maker.

10 g of Daqu was taken and dissolved in 100 ml of a sterile saline solution, and was shaker-oscillated for 30 min, then gradient dilution was performed, a WL solid flat plate was coated, a *Wickerhamomyces anomalus* single colony was selected for high-throughput liquid fermentation according to colonial morphological characteristics on the flat plate (FIG. 1), obtained potential low urea-producing *Wickerhamomyces anomalus* was subjected to molecular biological identification, 26S rDNA fragments of yeast were amplified respectively by utilizing yeast specific classification and identification primers NL1 and NL4, and gel electrophoresis detection was performed (FIG. 2). Then, sequencing alignment was performed to determine that screened low urea-producing yeast pertains to *Wickerhamomyces anomalus* taxonomically. Finally, a low urea-producing *Wickerhamomyces anomalus* strain was obtained, was named *Wickerhamomyces anomalus* CGMCC NO. 12416, and was deposited at China General Microbiological Culture Collection Center on May 6, 2016, with a deposit number of CGMCC NO. 12416.

WL medium: 4.0 g/L of yeast extract powder, 5.0 g/L of tryptone, 50.0 g/L of glucose, 0.55 g/L of potassium dihydrogen phosphate, 0.425 g/L of potassium chloride, 0.125 g/L of calcium chloride, 0.125 g/L of magnesium sulfate, 0.0025 g/L of ferric chloride, 0.0025 g/L of manganese sulfate, 20 g/L of agar and 22 mg/L of bromocresol green.

Embodiment 2: Function of Flavor Production by Strain Metabolism

Seed medium: a 25 ml test tube was taken, and was filled with 5 ml of a sorghum medium, and the *Wickerhamomyces anomalus* CGMCC NO. 12416 strain obtained in Embodiment 1 was inoculated, was treated under the conditions of natural pH, 30° C. and 200 rpm, and was aerobically cultured for 48 h.

Fermentation medium: a cultured seed culture solution was inoculated into a 250 ml triangular flask filled with 50 ml of a sorghum medium, was treated under the conditions of natural pH, inoculation amount of 5%, 30° C. and 200 rpm, and was fermented for 48 h.

Volatile products were analyzed by using a headspace solid-phase micro-extraction (HS-SPME) technology and a gas chromatography-mass spectrometry (GC-MS) method, 8 ml of a sample was taken and put into a headspace sampling bottle filled with 3 g of NaCl, and 10 μL of 4-methyl-2-pentanol with the concentration of 42.60 mg/L was added as an internal standard. The headspace sampling bottle was extracted for 45 min at 50° C., and after extraction is ended, GC-MS analysis was performed.

The flavor production ability of the strain obtained in Embodiment 1 by metabolism after 48 h of fermentation is shown in Table 1.

TABLE 1

| Flavor substance content (μg/L) | | | | | | |
|---|---|---|---|---|---|---|
| Alcohols | Esters | Ketones | Aldehydes | Benzene rings | Acids | Terpenes |
| 16365.08 | 239105.69 | 259.32 | 176.95 | 4623.65 | 165.23 | 150.23 |

Among main flavor substances, the contents of alcohols and esters are the most, where the alcohols contain 4324.18 μg/L of 3-methyl-1-butanol, 2653.32 μg/L of phenylethanol, 1232.68 μg/L of 2-methyl-1-propanol, 1564.12 μg/L of normal propanol, 3641.32 μg/L of isoamyl alcohol and 2976.32 μg/L of ethanol; the esters contain 147117.51 μg/L of ethyl acetate, which content is the most, followed by 31234.96 μg/L of 2-phenylethyl acetate, 2693.86 μg/L of ethyl propionate and 4569.32 μg/L of ethyl caproate.

Embodiment 3: Low Urea-Producing
*Wickerhamomyces anomalus* CGMCC NO. 12416

Seed medium: a 25 ml test tube was taken, and was filled with 5 ml of a sorghum medium, and the strain obtained in Embodiment 1 was inoculated, was treated under the conditions of natural pH, 30° C. and 200 rpm, and was aerobically cultured for 48 h.

Fermentation medium: a cultured seed culture solution was inoculated into a 250 ml triangular flask filled with 50 ml of a sorghum medium (500 mg/L of arginine precursor substance and 2% of ethanol were added), was treated under the conditions of inoculation amount of 5%, 30° C. and 200 rpm, and was fermented for 96 h. A yeast growth condition ($OD_{600}$) and a urea production condition in a fermentation process were determined. It was found that the strain entered a stable phase ($OD_{600}$: 1.8) after the fermentation process had been performed for 24 h, and a maximum value of urea yield achieved in the fermentation process was 227.42 μg/L (48 h).

Urea detection: the content of urea in fermentation broth was determined by using a high performance liquid chromatography-fluorescence detector (HPLC-FLD) coupled with precolumn derivatization. A specific operation includes: adding 500 ml of absolute ethanol, 400 μl of xanthydrol solution and 100 μl of 0.1 M hydrochloric acid solution to 500 μl of fermentation broth, shaking uniformly, and derivatizing at a room temperature for 30 min in the dark.

Embodiment 4: Comparison Between Urea
Production Conditions of *Wickerhamomyces
anomalus* CGMCC NO. 12416 and
*Wickerhamomyces anomalus* 21886

Seed medium: a 25 ml test tube was taken, and was filled with 5 ml of a sorghum medium, and the strain obtained in Embodiment 1 and a type strain *Wickerhamomyces anomalus* 21886 (deposited at China General Microbiological Culture Collection Center, with a strain number of 2.1886) were inoculated, were treated under the conditions of natural pH, 30° C. and 200 rpm, and were aerobically cultured for 48 h.

Fermentation medium: a cultured seed culture solution was inoculated into a 250 ml triangular flask filled with 50 ml of a sorghum medium (500 mg/L of arginine and 2% of ethanol were added), was treated under the conditions of inoculation amount of 5%, 30° C. and 200 rpm, and was fermented for 96 h. A yeast growth condition ($OD_{600}$) and a urea production condition in a fermentation process were determined. It was found that the ability of urea production of the *Wickerhamomyces anomalus* CGMCC NO. 12416 strain of the present invention in a fermentation process was obviously smaller than that of the type strain *Wickerhamomyces anomalus* 21886, a maximum value of urea production of the strain of the present invention in the fermentation process was 227.42 μg/L, and a maximum value of urea production of the type strain in the fermentation process was 3451.34 μg/L.

Urea detection: the content of urea in fermentation broth was determined by using a high performance liquid chromatography-fluorescence detector (HPLC-FLD) coupled with precolumn derivatization. A specific operation includes: adding 500 ml of absolute ethanol, 400 μl of xanthydrol solution and 100 μl of 0.1 M hydrochloric acid solution to 500 μl of fermentation broth, shaking uniformly, and derivatizing at a room temperature for 30 min in the dark.

Embodiment 5: Comparison Between Urea
Production Conditions of *Wickerhamomyces
anomalus* CGMCC NO. 12416 and Other Yeasts The present embodiment includes strains *Saccharomycopsis fibuligera, Millerozyma farinosa, Trichosporon asahii, Hanseniaspora osmophila, Pichia fermentans, Pichia membranifaciens* and *Clavispora lusitaniae*, as well as the strain *Wickerhamomyces anomalus* CGMCC NO. 12416 of the present invention. The seven strains come from a Chinese liquor fermentation environment.

Seed medium: a 25 ml test tube was taken, and was filled with 5 ml of a sorghum medium, and the *Wickerhamomyces anomalus* CGMCC NO. 12416 as well as *Wickerhamomyces anomalus, Saccharomycopsis fibuligera, Millerozyma farinosa, Saccharomyces cerevisiae, Trichosporon asahii, Hanseniaspora osmophila, Pichia fermentans, Pichia membranifaciens* and *Clavispora lusitaniae* were inoculated, were treated under the conditions of natural pH, 30° C. and 200 rpm, and were aerobically cultured for 48 h.

Fermentation medium: a cultured seed culture solution was inoculated into a 250 ml triangular flask filled with 50 ml of a sorghum medium (500 mg/L of arginine and 2% of ethanol were added), was treated under the conditions of inoculation amount of 5%, 30° C. and 200 rpm, and was fermented for 96 h. A yeast growth condition ($OD_{600}$) and a urea production condition in a fermentation process were determined. By comparing the yield of urea fermented for 6 h and $OD_{600}$, it was found that the yields of urea of these eight strains within a unit time during fermentation for 6 h respectively were as follows: 100 to 500 μg/OD of *Wickerhamomyces anomalus* CGMCC NO. 12416, 1300 to 2500 μg/OD of *Millerozyma farinose* and *Trichosporon asahii*, and yields of the rest strains being greater than 3000 μg/OD.

This shows that the ability of the strain *Wickerhamomyces anomalus* CGMCC NO. 12416 of the present invention to produce urea is obviously less than that of other yeasts obtained by isolating from a fermentation environment of Chinese liquor.

Embodiment 6: Physiological and Biochemical Properties of Strains

With a growth temperature range of 4 to 48° C., a suitable temperature of 25 to 33° C. and a growth pH range of 2.3 to 12.0, preferably 4.0 to 8.0, growing in an environment containing 60% of glucose, 2.0% of KCl and 12% of ethanol was possible.

The *Wickerhamomyces anomalus* CGMCC NO. 12416 strain obtained in Embodiment 1 was inoculated in a YPD liquid medium, was cultured for 24 h at 30° C., and then was diluted by using a sterile saline solution to achieve $OD_{600}$ of 1, and 0.5 ml of a bacterial solution was extracted into 50 ml of a tolerance medium.

Temperature tolerance medium: a YPD medium, wherein. static culture was performed for 48 h at 30° C., 37° C., 40° C., 42° C. and 46° C. respectively. Results showed that the *Wickerhamomyces anomalus* CGMCC NO. 12416 strain of the present invention can be grown in a temperature range of 28 to 46° C.

Acid tolerance medium: a YPD medium, wherein a pH of the medium was regulated by using 0.1M lactic acid to 2.9, 2.7, 2.5, 2.4 and 2.3 respectively, and static culture was performed for 48 h at 30° C. Results showed that the *Wickerhamomyces anomalus* CGMCC NO. 12416 strain of the present invention can be grown in a pH range of 2.9 to 2.3.

Alcohol content tolerance medium: a YPD medium, wherein ethanol was added to make the alcohol content reach 0, 4%, 6%, 8%, 10%, 12% and 14% respectively, and static culture was performed for 48 h at 30° C. Results showed that the *Wickerhamomyces anomalus* CGMCC NO. 12416 strain of the present invention can be grown in an alcohol content range of 0 to 12%.

Sugar content tolerance medium: a YPD medium, wherein different masses of glucose were added to make glucose concentration reach 1%, 40%, 50%, 60%, 65% and 70% respectively, and static culture was performed for 48 h at 30° C. Result showed that the *Wickerhamomyces anomalus* CGMCC NO. 12416 strain of the present invention can be grown in a glucose concentration range of 0 to 60%.

Osmotic pressure tolerance medium: a YPD medium, wherein different masses of KCl were added to make KCl concentration reach 0, 0.7 mol/L, 1 mol/L, 1.4 mol/L, 1.7 mol/L and 2 mol/L, and static culture was performed for 48 h at 30° C. Results showed that the *Wickerhamomyces anomalus* CGMCC NO. 12416 strain of the present invention can be grown in a KCl range of 0 to 2 mol/L.

Embodiment 7: Use of *Wickerhamomyces anomalus* CGMCC NO. 12416 in Sesame-Flavored Chinese Liquor The *Wickerhamomyces anomalus* CGMCC NO. 12416 strain of the present invention was prepared into a liquid inoculant. A preparation method therefor includes: inoculating the *Wickerhamomyces anomalus* CGMCC NO. 12416 strain in a liquid yeast inoculant medium, and culturing for 24 h at 30° C., a recipe for the liquid yeast inoculant medium being A or B, wherein A: 10 g/L of yeast extract, 20 g/L of peptone, 20 g/L of glucose and the balance of water were contained.

B: Raw materials used for Chinese liquor fermentation were medium components. After the raw materials were crushed, the raw materials were mixed in a ratio of the raw materials to water being 1:1 to 1:4 w/v, and were cooked for 1 to 5 h. After cooling, a raw material namely 10 to 50 units/g of glucoamylase was added, an obtained material was kept for 2 to 10 h at 40 to 80° C., and was filtered and centrifuged to obtain filtrate, a sugar content was adjusted to 10 to 150 Bx, and a pH was adjusted to 4 to 6, wherein the raw materials were any one or a mixture of more of sorghum, barley, wheat, peas and bran in any proportion.

The liquid inoculant was added into raw materials for making sesame-flavored liquor bran starter, after the bran starter was made, the bran starter was added into fermented grains for fermentation, after the fermentation was finished, the contents of urea and EC in fermented grains at the later stage of fermentation for base liquor production and in raw wine were detected, and it was found that the bran starter with added *Wickerhamomyces anomalus* CGMCC NO. 12416 can remarkably reduce the content of urea in the fermented grains and the raw wine by 20 to 50% during production. Meanwhile, the reduction amount of EC was in a range of 15 to 45%, the reduction amount of EC in the raw wine was in a range of 15 to 35%, and it was shown that the contents of urea and EC in food can be truly reduced by adding the strain of claim 1.

What is claimed is:

1. A method of preparing food, comprising:
preparing a culture by inoculating into a yeast medium an inoculum of live culture of *Wickerhamomyces anomalus* strain CGMCC NO. 12416, wherein the yeast medium comprises yeast extract, peptone, and glucose;
incubating the culture at 30° C. to stimulate growth of the *W. anomalus*;
adding the culture to a liquor fermentation medium, wherein the liquor fermentation medium comprises active glucoamylase enzyme and a mixture of one or more of sorghum, barley, wheat, peas, and bran; and
incubating the liquor fermentation medium with heat thereby fermenting the liquor fermentation medium in the presence of the culture;
wherein incubating is discontinued before urea concentration in the liquor fermentation medium reaches 351.23 μg/L;
wherein the *W. anomalus* CGMCC NO. 12416 strain is deposited at China General Microbiological Culture Collection Center on May 6, 2016, with a deposit number of CGMCC NO. 12416.

2. The method of claim 1, wherein the food is liquor, wine, yellow rice wine or fruit wine.

3. The method of claim 1, wherein the liquor fermentation medium is a bran starter, and the method comprises adding the culture of the Wickerhamomyces anomalus CGMCC NO. 12416 strain into the bran starter of a sesame-flavored liquor, and then adding the bran starter into fermented grains for fermentation.

* * * * *